United States Patent
Shi

(10) Patent No.: US 10,420,473 B2
(45) Date of Patent: Sep. 24, 2019

(54) WEARABLE THERMOMETER PATCH FOR CORRECT MEASUREMENT OF HUMAN SKIN TEMPERATURE

(71) Applicant: VivaLnk Inc., Santa Clara, CA (US)

(72) Inventor: Wei Shi, San Jose, CA (US)

(73) Assignee: VivaLnk, Inc., Campbell, CA (US)

( * ) Notice: Subject to any disclaimer, the term of this patent is extended or adjusted under 35 U.S.C. 154(b) by 379 days.

(21) Appl. No.: 15/406,380

(22) Filed: Jan. 13, 2017

(65) Prior Publication Data

US 2018/0028070 A1  Feb. 1, 2018

Related U.S. Application Data

(63) Continuation-in-part of application No. 15/224,121, filed on Jul. 29, 2016, now abandoned.

(51) Int. Cl.
*A61B 5/01* (2006.01)
*A61B 5/00* (2006.01)

(52) U.S. Cl.
CPC .............. *A61B 5/01* (2013.01); *A61B 5/0008* (2013.01); *A61B 5/6833* (2013.01); *A61B 5/6843* (2013.01); *A61B 2560/0412* (2013.01)

(58) Field of Classification Search
CPC ....... A61B 5/01; A61B 5/0008; A61B 5/6843; G01K 7/00; G01K 7/42; G01K 1/16; G01K 1/165; G01K 1/20; G01K 1/24; G01K 13/002
See application file for complete search history.

(56) References Cited

U.S. PATENT DOCUMENTS

| 5,294,200 | A | * | 3/1994 | Rall | G01K 1/16 374/120 |
| 5,853,409 | A | * | 12/1998 | Swanson | A61B 18/00 606/31 |
| 2004/0076215 | A1 | * | 4/2004 | Baumbach | G01K 1/16 374/29 |
| 2007/0239038 | A1 | * | 10/2007 | Nicolaescu | A61B 5/01 600/483 |
| 2007/0270672 | A1 | | 11/2007 | Hayter | |
| 2007/0282218 | A1 | * | 12/2007 | Yarden | G01K 1/165 600/549 |
| 2009/0171180 | A1 | | 7/2009 | Pering | |
| 2012/0109572 | A1 | * | 5/2012 | Shimizu | G01K 1/165 702/131 |
| 2012/0242481 | A1 | | 9/2012 | Gernandt | |
| 2014/0121557 | A1 | * | 5/2014 | Gannon | A61B 5/002 600/549 |
| 2015/0055681 | A1 | * | 2/2015 | Tsuchida | G01K 7/427 374/183 |
| 2017/0086743 | A1 | * | 3/2017 | Bushnell | A61B 5/6843 |

* cited by examiner

*Primary Examiner* — Daniel L Cerioni
*Assistant Examiner* — Raymond P Dulman
(74) *Attorney, Agent, or Firm* — SV Patent Service

(57) ABSTRACT

A wearable thermometer patch includes a substrate and a temperature probe unit mounted in the substrate and configured to measure temperature of a user's skin. The temperature probe unit includes a force sensor configured to measure contact force between the temperature probe unit and the user' skin, a plate, a first temperature sensor attached to a lower surface of the plate, and a second temperature sensor attached to an upper surface of the plate.

14 Claims, 7 Drawing Sheets

WEARABLE THERMOMETER PATCH FOR CORRECT MEASUREMENT OF HUMAN SKIN TEMPERATURE

BACKGROUND OF THE INVENTION

The present application relates to electronic devices, and in particular, to electronic patches that can attach to human skin for conducting measurement.

Electronic patches can be used for tracking objects and for performing functions such as producing sound, light or vibrations, and so on. As applications and human needs become more sophisticated and complex, electronic patches are required to perform a rapidly increasing number of tasks. Electronic patches are often required to be conformal to curved surfaces, which in the case of human body, can vary overtime.

Electronic patches can communicate with smart phones and other devices using WiFi, Bluetooth, Near Field Communication (NFC), and other wireless technologies. NFC is a wireless communication standard that enables two devices to quickly establish communication within a short range around radio frequency of 13.56 MHz. NFC is more secure than other wireless technologies such as Bluetooth and Wi-Fi because NFC requires two devices in close proximity (e.g. less than 10 cm). NFC can also lower cost comparing to other wireless technologies by allowing one of the two devices to be passive (a passive NFC tag).

Bluetooth is another wireless communication standard for exchanging data over relatively longer distances (in tens of meters). It employs short wavelength UHF radio waves from 2.4 to 2.485 GHz from fixed or mobile devices. Bluetooth devices have evolved to meet the increasing demand for low-power solutions that is required for wearable electronics. Benefited from relatively longer reading distance and active communication, Bluetooth technologies allow wearable patches to continuously monitoring vital information without human interference, which is an advantage over NFC in many applications.

Wearable patch (or tag) is an electronic patch to be worn by a user. A wearable patch is required to stay on user's skin and operate for an extended period of time from hours to months. A wearable patch can contain a micro-electronic system that can be accessed using NFC, Bluetooth, WiFi, or other wireless technologies. A wearable patch can be integrated with different sensors such as vital signs monitoring, motion track, skin temperature measurements, and ECG detection.

Despite recent development efforts, current wearable patches still suffer several drawbacks: they may not provide adequate comfort for users to wear them; they may not stay attached to user's body for the required length of time; and they are usually not aesthetically appealing. The conventional wearable patches also include rigid polymer substrates that are not very breathable. The build-up of sweat and moisture can cause discomfort and irritation to the skin, especially after wearing it for an extended period of time.

Conventional wearable thermometer patches have the additional challenge of inaccurate temperature measurement due to factors such as thermal resistance between the temperature sensor and the human skin, conduction loss of the temperature sensor to the ambient environment, as well as temperature reduction in the user skin caused by the thermal conduction to the wearable patch. Moreover, conventional wearable thermometer patches can also have slow measurement responses.

Another challenge for conventional wearable thermometer patches is that the user's skin may interfere with their proper wireless communications. For example, the antenna's communication range can be significantly reduced by the adjacency to user's skin. The wireless communication range of an antenna in contact with the skin is less than half the range for an antenna that is placed 4 mm away from the user's skin.

Another challenge is that it is extremely difficult to measure the surface temperature accurately, especially when measuring the human skin temperature which being impacted by the blood circulation under the skin. Several critical factors can impact the continuous measurement of armpit temperature: the ambient temperature can impact temperature measurement when arm is opened; and thermal contact resistance can change when the contact between the temperature probe and human skin became loose.

There is therefore a need for a flexible wearable electronic patch that can correctly measure temperatures of user's skin with high accuracy and fast response time, while capable of performing wireless communications in a required range.

SUMMARY OF THE INVENTION

The presently disclosure attempts to address the aforementioned limitations in conventional electronic patches. The presently disclosed wearable wireless thermometer patch that can be attached to human skin to conduct temperature measurements with high accuracy and faster respond time.

In the presently disclosed wearable wireless thermometer patch, temperature measurement errors due to the thermal noise from the environment are minimized. In metrology, accurate metrology instrument is associated with high Signal-to-Noise Ratio (SNR). In the presently disclosed wearable thermometer patch, the thermal resistance between the temperature sensor and the human skin is minimized, so that the maximum amount of heat can be conducted quickly from the user skin to the temperature sensor. Moreover, the heat conduction loss from the temperature sensor to the ambient is also minimized by the structure design and thermal material. Furthermore, a perforated protective film is placed between the user skin and the body of the wearable patch to reduce the heat conduction from the user skin, because the conventional non-perforated film will lower down the true temperature of the skin due to the attachment of the wearable patch. In addition, the presently disclosed wearable thermometer patch is structured to have low thermal capacity which results in faster responding time as well as higher flexibility.

Furthermore, the disclosed electronic patches are also breathable and stretchable. The stretchability and the breathability make the disclosed electronic patches more comfortable for the users. The disclosed electronic patches are capable wireless communication with little interference from users' skins. Moreover, the disclosed electronic patches can conduct measurements both at users' skins and away from the user's skin. The present application further discloses simple and effective manufacturing process to fabricate such wearable electronic patches.

Additionally, the disclosure teaches a wearable wireless thermometer patch structure that can be attached to human skin for the correct temperature measurement with the double temperature sensors (DTS) and a force sensor. Using DTS, the temperature under the dermis can be easily calculated from the Fourier's Law at the thermal equilibrium status, which is independent of the ambient temperature changes when the arm is open or closed. By integrating the force sensor, the thermal contact resistance can be easily correlated to the contacting force, from which the armpit temperature can be calculated more accurately regardless the arm is lightly or tightly in contact with the thermometer patch.

In one general aspect, the present invention relates to a wearable thermometer patch that includes a substrate and a temperature probe unit mounted in the substrate and configured to measure temperature of a user's skin. The temperature probe unit can include a force sensor configured to measure contact force between the temperature probe unit and the user' skin, a plate, a first temperature sensor attached to a lower surface of the plate, and a second temperature sensor attached to an upper surface of the plate.

Implementations of the system may include one or more of the following. The substrate can include an electric circuit that is electrically connected to the first temperature sensor, the second temperature sensor, and the force sensor. The first temperature sensor and the second temperature sensor can be respectively configured to measure a first time series of temperature values and a second time series of temperature values, wherein the temperature of the user's skin is calculated by discarding at least a portion of the temperature values in the first time series of temperature values and the second time series of temperature values based on the contact force measured by the force sensor. The substrate can include an opening, wherein the temperature probe unit comprises a thermally conductive cup having a bottom portion mounted in the opening of the substrate. The wearable thermometer patch can further include a thermally-conductive adhesive that fixes the first temperature sensor, the second temperature sensor, and the plate to an inner surface of the thermally conductive cup. The wearable thermometer patch can further include a thermally insulating material in a top portion of the thermally conductive cup, wherein the force sensor is positioned on the thermally insulating material and the thermally conductive cup. The wearable thermometer patch can further include a controller mounted on the flexible circuit substrate and in electric connection with the electric circuit, wherein the controller can receive first electric signals from the first temperature sensor and the second temperature sensor in response to respective temperature measurements, wherein the controller can receive second electric signals from the force sensor in response to measurement of the contact force. The controller can calculate the temperature of the user's skin using a difference between temperature measurements from the first temperature sensor and the second temperature sensor. The controller can segment a time series of the temperature measurements from the first temperature sensor and the second temperature sensor based on the second electric signals received from the force sensor. The controller can calculate the temperature of the user's skin by discarding at least a portion of the temperature values in the first time series of temperature values and the second time series of temperature values based on the contact force measured by the force sensor. The wearable thermometer patch can further include an antenna in electric connection with the semiconductor chip, wherein the antenna to wirelessly send measured temperature values and contact force values to an external device. The wearable thermometer patch can further include electronic components mounted or formed on the flexible circuit substrate and in electric connection with electric circuit, wherein the electronic components can include a semiconductor chip, an antenna, a battery, or a bonding pad. The wearable thermometer patch can further include an elastic layer formed on the substrate and the temperature probe unit. The wearable thermometer patch can further include an adhesive layer under the substrate, the adhesive layer configured to attach to human skin.

These and other aspects, their implementations and other features are described in detail in the drawings, the description and the claims.

DETAILED DESCRIPTION OF THE INVENTION

Figure 1:
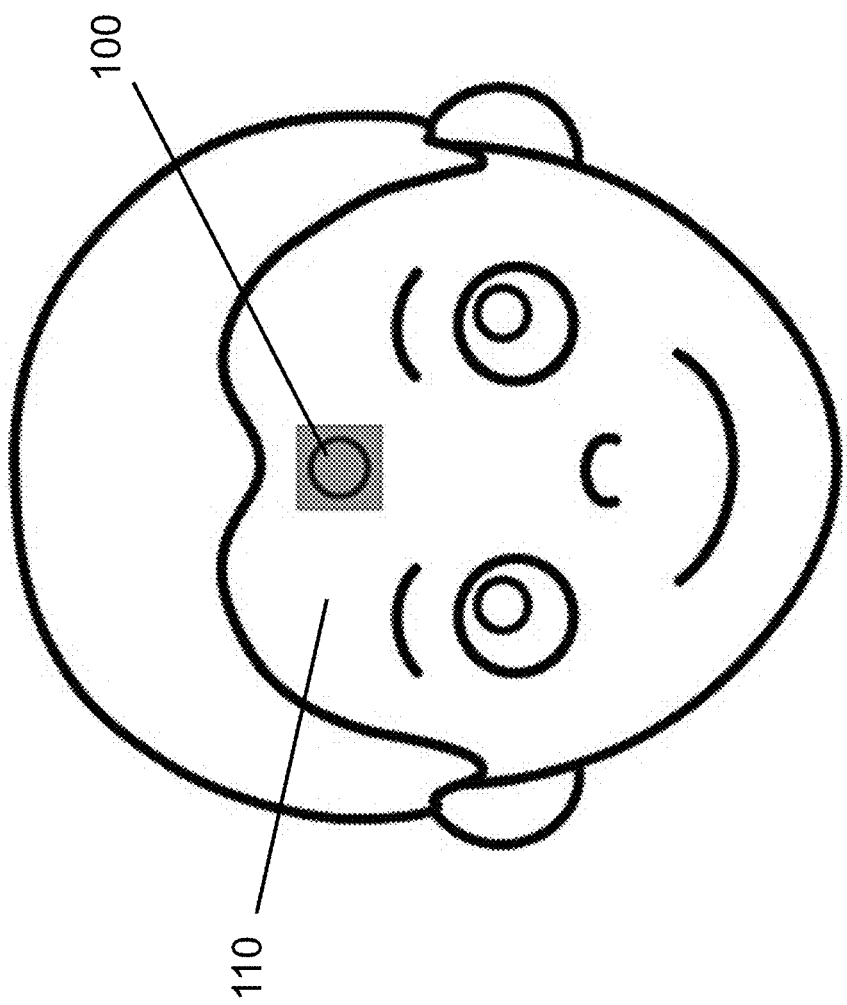
FIG. 1 illustrates the usage of a wearable patch attached to a user's skin.

Referring to FIG. 1, a wearable patch 100 is attached to a user's skin 110 for measuring body vital signs. The wearable patch 100 can be placed on forehead, hand, wrist, arm, shoulder, waist, leg, foot, or other parts of the body. In the present disclosure, the term "wearable patch" can also be referred to as "wearable sticker" or "wearable tag".

As discussed above, wearable electronic patches face several challenges: the user's skin 110 may interfere with their proper operations. For example, the wearable patch 100 may include an antenna for wireless communications with other devices. The antenna's communication range can be significantly reduced when an antenna is placed in contact with the user's skin 110.

The presently disclosure aims to overcome the drawbacks in conventional wearable patches, and to provide highly stretchable, compliant, durable, breathable, and comfortable wearable electronic patches while performing more accurate and more responsive measurements and communication functions.

Figure 2:
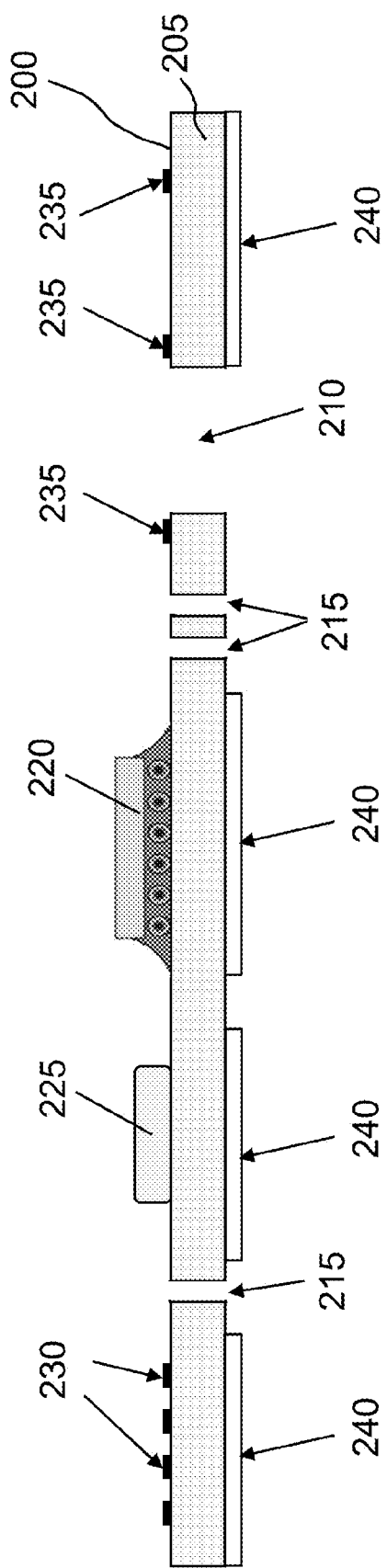
FIG. 2 is a cross-sectional view of a base structure for constructing a wearable thermometer patch in accordance with some embodiments of the present invention.

Referring to FIG. 2, a base structure 200 includes a flexible circuit substrate 205 having an electric circuit embedded in or formed on. The flexible circuit substrate 205 has a large opening 210 and multiple small through holes 215. A semiconductor chip 220, a battery 225, an antenna 230, and bonding pads 235 are mounted or formed on the upper surface of the flexible circuit substrate 205. The semiconductor chip 220, the battery 225, the antenna 230, and at least one of the bonding pads 235 is connected with the electric circuit in the flexible circuit substrate 205.

Stiffening layers 240 are formed on the layer surface of the flexible circuit substrate 205 at locations respectively below electronic components such as the semiconductor chip 220, the battery 225, the antenna 230, and the bonding pads 235. The stiffening layers 240 have higher Young's modulus than that of the flexible circuit substrate 205, and can protect the electronic devices from being damaged when the flexible circuit substrate 205 is bent. The flexible circuit substrate 205 can be made of polymeric materials and built in with electric circuitry that connects the semiconductor chip 220, the battery 225, the antenna 230, and the bonding pads 235. The stiffening layers 240 can be made of metallic or polymeric materials.

Figure 3:
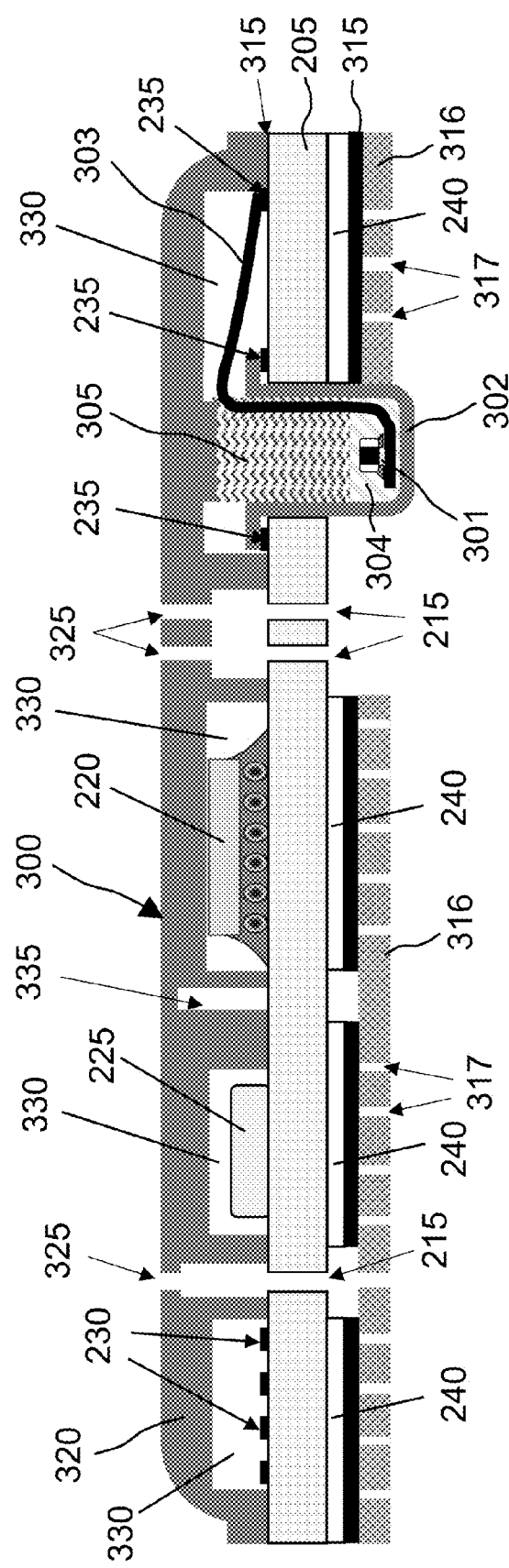
FIG. 3 is a cross-sectional view of a wearable thermometer patch capable of conducting accurate and fast-response temperature measurements and effective wireless communications in accordance with some embodiments of the present invention.
Figure 4:
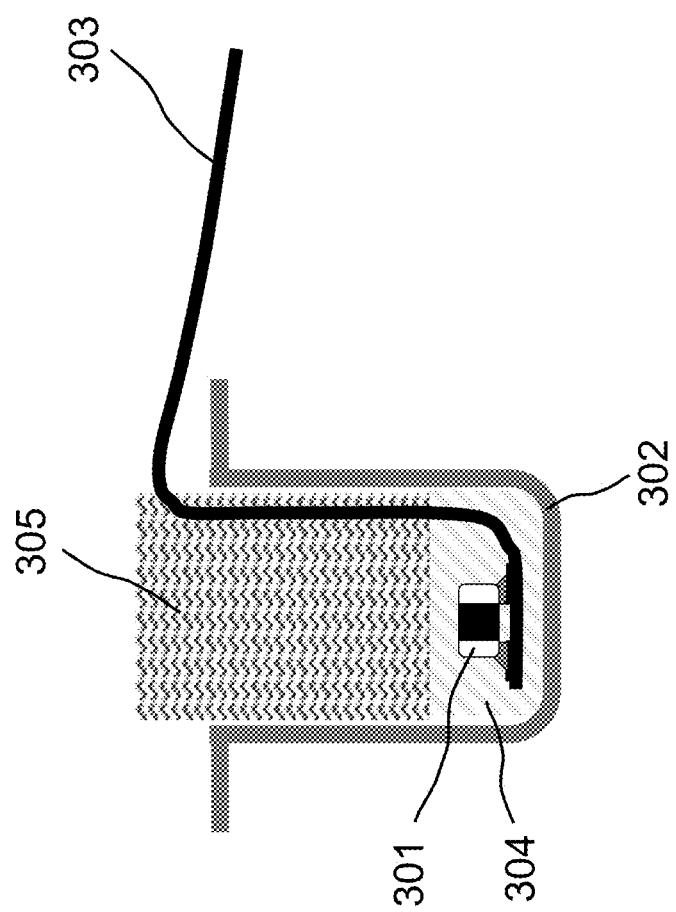
FIG. 4 is a detailed cross-sectional view of the temperature sensing portion in the wearable thermometer patch in FIG. 3.

Referring to FIGS. 3 and 4, a wearable thermometer patch 300 that includes an assembly for temperature sensing, in addition to the components in the base structure 200 as shown in FIG. 2. A thermally conductive cup 302 has its bottom portion plugged into the large opening 210 (FIG. 2). The bottom portion of the thermally conductive cup 302 protrudes out of the lower surface of the flexible circuit substrate 205. The lips of the thermally conductive cup 302 near its top portion are fixedly attached or bonded to bonding pads 235 by soldering or with an adhesive. The thermally conductive cup 302 can be made of a thermally conductive metallic or alloy material such as copper, stainless steel, ceramic or carbide composite materials. A temperature sensor 301 is attached to and in thermal conduction with an inner surface near the bottom of the thermally conductive cup 302. The temperature sensor 301 can be implemented, for example, by a Thermistor, a Resistor Temperature Detector, or a Thermocouple. When an outer surface of the bottom portion of the thermally conductive cup 302 is in contact with a user's skin, the thermally conductive cup 302 can thus effectively transfer heat from a user's skin to the temperature sensor 301. A flexible conductive ribbon 303 is connected to the temperature sensor 301 in the thermally conductive cup 302 and one of the conductive pads 235 on the flexible circuit substrate 205. Thus the temperature sensor 301 is connected to the electric circuit in the flexible circuit substrate 205 and can send an electric signal to the electric circuit and the semiconductor chip 220 in response to temperature measured by the temperature sensor 301. The semiconductor chip 220 processes the electric signal and output another electrical signal which enables the antenna 230 to transmit a wireless signal to send measurement data to another external device such as a mobile phone or a computer. The battery 225 powers the semiconductor chip 220, the electric circuit, and possibly the temperature sensor 301.

The temperature sensor 301 and a portion of the flexible conductive ribbon 303 are fixed to an inner surface at the bottom of the thermally conductive cup 302 by a thermally-conductive adhesive 304, which allows effective heat transfer from the bottom of the thermally conductive cup 302 to the temperature sensor 301. Examples of the thermally-conductive adhesive 304 can include electrically-insulative thermally-conductive epoxies and polymers. A thermally insulating material 305 is fixed in and fills the top portion of the thermally conductive cup 302, which fixes the thermally-conductive adhesive 304 at the bottom of the thermally conductive cup 302 and reduces heat loss from the temperature sensor 301 to the elastic layer (described below) or the environment. The flexible conductive ribbon 303 can be bent and laid out along the wall the thermally conductive cup 302.

A layer of a perforated polymer material 316 is bonded to the bottom surface of the flexible circuit substrate 205 using adhesive material 315. Suitable material for the perforated polymer material 316 can include soft materials such as Polyurethane. The layer of perforated polymer material 316 can include multiple holes 317: one of them exposes a bottom of the thermally conductive cup; others allow sweat and moisture to escape through holes 215 and holes 325; while other holes 317 help enhance flexibility and comfort of the perforated polymer material. An adhesive material is applied to the lower surface of the perforated polymer material 316 to be attached the lower surface of the perforated polymer material 316 to the user's skin, so that the bottom of the thermally conductive cup 302 can be in tight contact with a user's skin for the accurate temperature measurement of the user's skin.

It should be noted that when the wearable thermometer patch 300 is worn by the user, the antenna 230 is separated from the user's skin by the flexible circuit substrate 205 and the layer of the perforated polymer material 316, which minimizes the impact of the user's body on the transmissions of wireless signals by the antenna 230.

An elastic layer 320 is bonded onto the upper surface of the flexible circuit substrate 205 with an adhesive material 315 in between. Alternatively, the elastic layer 320 can directly be molded onto the flexible circuit substrate 205 without using any bonding interface material 315. The elastic layer 320 includes recesses 330 on the underside to define cavities to contain the antenna 230, the battery 225, the semiconductor chip 220 and the flexible conductive ribbon 303. The elastic layer 320 also includes holes 325 that are registered to the through holes 215 in the flexible circuit substrate 205, which allows moisture and sweat from the user's skin to diffuse to the ambient environment, which enhances user's comfort and strength of attachment of the wearable thermometer patch 300 to the user's skin. The elastic layer 320 can include one or more cavities 335 for enhancing flexibility (bendable) and stretchability of the elastic layer 320 and the whole wearable thermometer patch 300. The cavities 335 can have elongated shapes with lengthwise direction oriented perpendicular to the flexible circuit substrate 205.

The elastic layer 320 can be made of a non-conductive material such as an elastomeric material or a viscoelastic polymeric material having low Young's modulus and high failure strain. In some embodiments, the elastic layer 320 has a Young's Modulus<0.3 Gpa. In some cases, the elastic layer 320 and can have Young's Modulus<0.1 Gpa to provide enhanced flexibility and tackability. Materials suitable for the elastic layer 320 include elastomers, viscoelastic polymers, such as silicone, silicone rubber, and medical grade polyurethane that is a transparent medical dressing used to cover and protect wounds with breathability and conformation to skin.

The disclosed wearable thermometer patch can significantly enhance measurement accuracy and responsiveness, and reduce thermal noise. The temperature sensor is positioned very close to a user's skin. The temperature sensor is placed at the bottom of a thermally conductive cup and in good thermal conduction with the user's skin. The minimized thermal resistance between the temperature sensor and the user's skin reduces temperature measurement error and also decreases measurement response time. Moreover, the temperature sensor is secured fixed by an adhesive to the bottom of the thermally conductive cup such that the temperature sensor is not affected and detached by user's body movements, which improves durability of the wearable thermometer patch. Furthermore, the temperature sensor is thermally isolated with the ambient environment by a thermal insulating material in the top portion of the thermally conductive cup. The reduced thermal capacity helps further reduces background noise in the measurements of user's skin temperature and increase response rate of measurement. A layer of soft perforated polymer material under the flexible substrate minimizes heat conduction from the user's skin to the wearable thermometer patch, thus reducing the "cooling effect" of the user's skin by the wearable thermometer patch.

Another advantage of the disclosed wearable thermometer patch is that it is stretchable, compliant, durable, and comfortable to wear by users. The disclosed wearable thermometer patch includes a flexible substrate covered and protected by an elastic layer that increases the flexibility and stretchability. Cavities within the elastic layer further increase its flexibility and stretchability. A layer of soft perforated polymer material under the flexible substrate provides comfortable contact to user's skin is in contact with user's skin. Openings in the elastic layer, the substrate, and the soft perforated polymer material can bring moisture and sweat from the user's skin to the ambient environment, which increases user's comfort as well as strength of the attachment of the wearable thermometer patch to user's skin.

Yet another advantage of the disclosed wearable thermometer patch is that it can significantly increase wireless communication range by placing the antenna on the upper surface of the flexible circuit substrate. The thickness of the substrate as well as the height of the thermally conductive cup can be selected to allow enough distance between the antenna and the user's skin to minimize interference of user's body to the wireless transmission signals.

Further details of wearable thermometer patches are disclosed in the commonly assigned co-pending U.S. patent application Ser. No. 14/814,347 "Three dimensional electronic patch", filed Jul. 30, 2015, the disclosure of which is incorporated herein by reference.

In some embodiments, the present disclosure teaches an improved thermometer patch that can properly compensate for the status of the physical contacts (no contact, loose contact, or tight contact, etc.) between the thermometer patch and the user's body.

Figure 5:
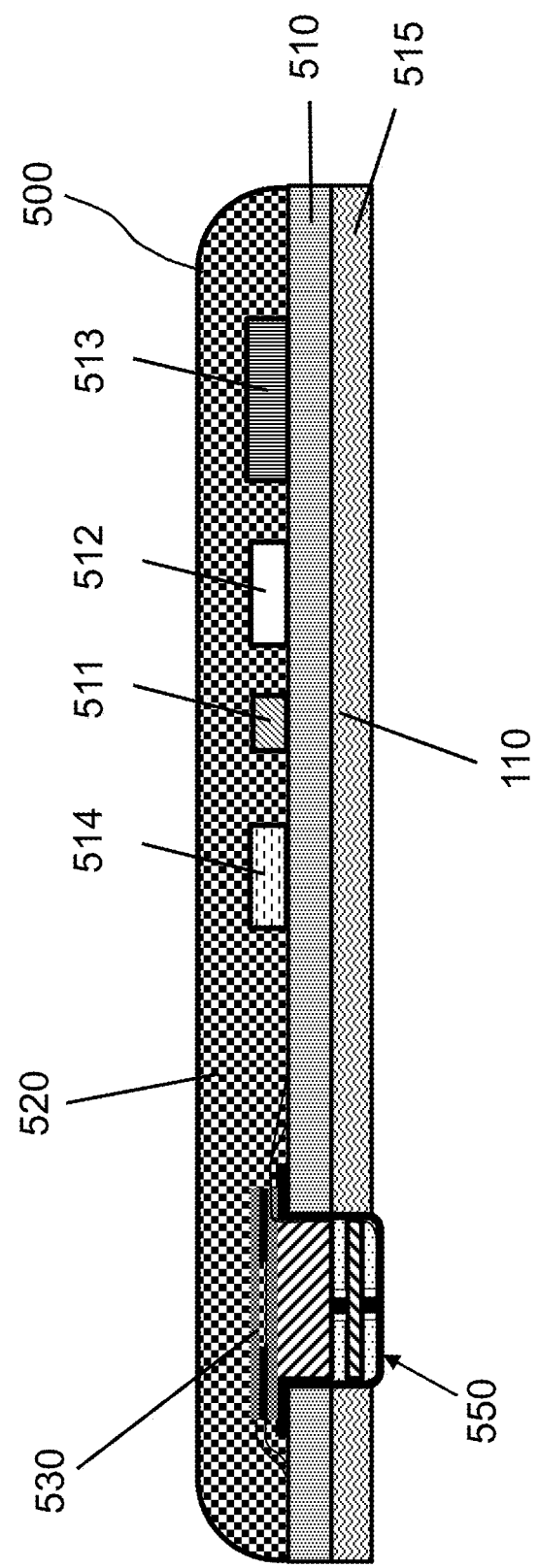
FIG. 5 is a cross-sectional view of an improved wearable thermometer patch including a DTS and a force sensor to assist correct temperature measurements in accordance with some embodiments of the present invention.
Figure 6:
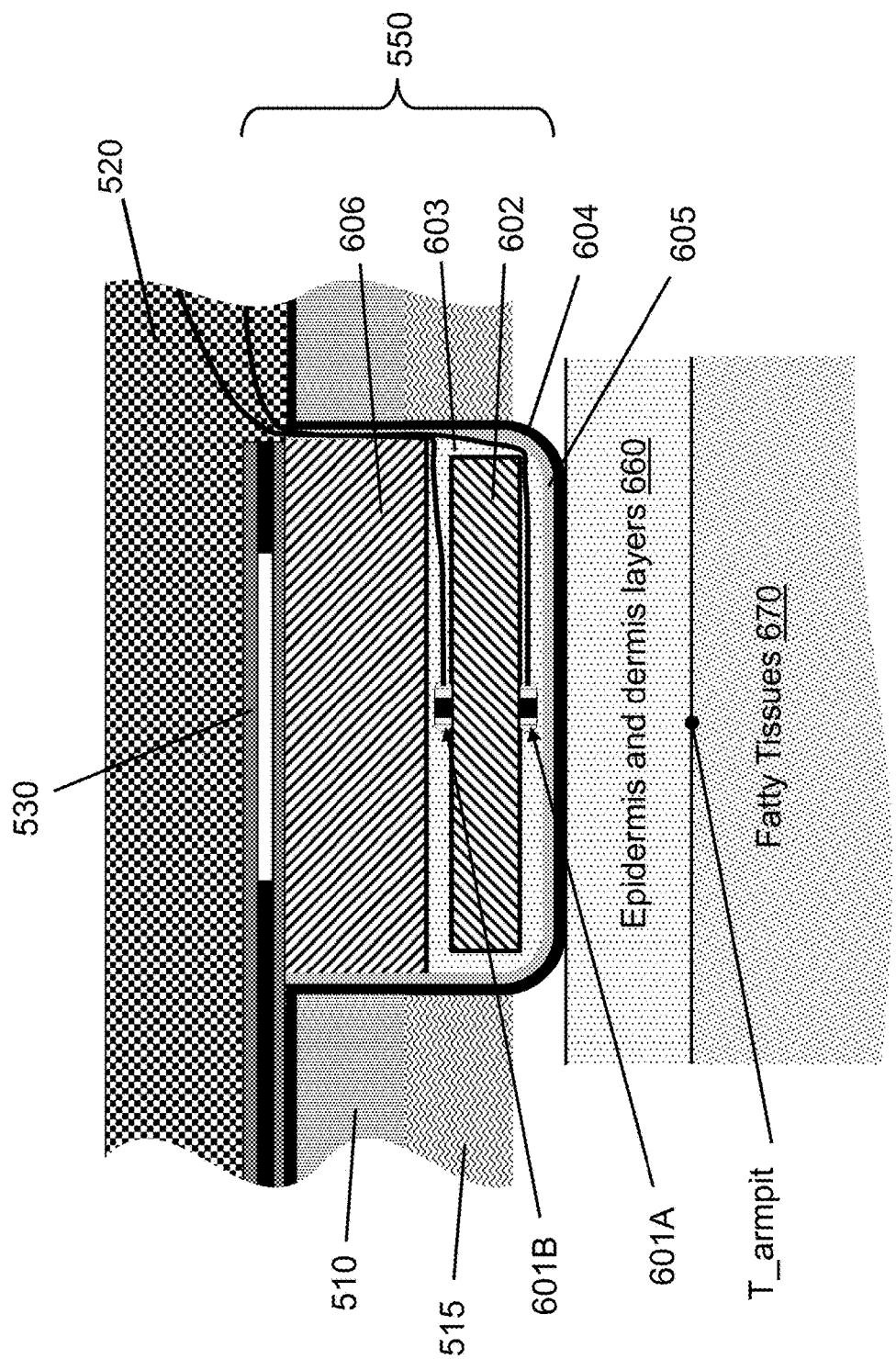
FIG. 6 is a detailed cross-sectional view of the temperature sensing portion in the wearable thermometer patch shown in FIG. 5.

Referring to FIGS. 5 and 6, an improved wearable thermometer patch 500 includes a temperature probe unit 550, a substrate 510, and a RF antenna 511, a Bluetooth chip 512, a battery 513, and a controller 514 mounted on the substrate 510. An adhesive layer formed under the substrate 510 can attach the improved wearable thermometer patch 500 to human skin. The substrate 510 can be implemented by a flexible printed circuit board (PCB), a printed PET, or a PCB). The RF antenna 511, the Bluetooth chip 512, the battery 513, and the controller 514 are electrically connected a circuit (not shown) in the substrate 510. An elastic layer 520 is formed on the temperature probe unit 550, the substrate 510, the RF antenna 511, the Bluetooth chip 512 and the battery 513. The elastic layer 520 can be formed by materials such as silicone, polyurethane, thermoplastic polyurethane, a polyethylene foam, or a fabric.

The temperature probe unit 550 includes temperature sensors 601A and 601B which are respectively bonded to the bottom surface and the top surface of a plate 602. The plate 602 has a known thermal resistance, which can be formed by materials such as plastic, ceramic, metal, or foam materials. The temperature sensors 601A and 601B can be implemented for example by thermistor, a resistance temperature detector, or thermocouple, which are electrically connected to the circuit in the substrate 510. The temperature probe unit 550 also includes a metal cup 604 which is mounted in an opening in the substrate 510. The metal cup 604 can be formed with copper, stainless, ceramic, carbide, or other metallic alloys. An electrically insulating layer 605 is formed on an inner surface of the metal cup 604. The assembly of temperature sensors 601A and 601B and the plate 602 are attached to the metal cup 604 and the electrically insulating layer 605 therein by thermally-conductive epoxy 603. A thermally insulating material 606 fills up the metal cup 604 over the thermally-conductive epoxy 603.

The temperature probe unit 550 also includes a force sensor 530 attached to the top of the metal cup 604 and the thermally-insulating material 606 therein. The force sensor 530 is electrically connected to the circuit in the substrate 510, and can be implemented by a force sensitive resistor (FSR), a micromechanical electro (MEMS) strain sensor, or other types of force or pressure sensors. The elastic layer 520 is compressible when an external force is applied to the top of the improved wearable thermometer patch 500, which transmits a force to the force sensor 530.

When the improved wearable thermometer patch 500 is attached to a user's skin under the armpit, it is desirable to accurately measure the user's body temperature under the skin, at the interface between epidermis and dermis layers 660 and a fatty tissue layer 670.

In accordance with the present invention, the assembly of temperature sensors 601A and 601B and the force sensor 530 allows accurate measurement of the user's skin temperature. When the diameter of a plate is large enough, the temperature distribution across the surfaces is approximately uniform; one-dimensional Fourier's law can be applied to describe heat conduction in the thickness direction of the plate 602:

$$q = K(T1-T2)/\Delta x \qquad \text{eqn (1)}$$

where q is the heat flux conducted through the plate; K is the thermal conductivity of the plate 602; T1 and T2 are respectively the temperatures measured by the temperature sensors 601A and 601B at the bottom and the top surfaces of the plate 602, while $\Delta x$ is the thickness of the plate 602.

The epidermis and dermis layers 660, the bottom layer of the metal cup 604, the electrically insulating layer 605, and the layer of thermally-conductive epoxy 603 between the temperature sensor 601A and the electrically insulating layer 605 can also be modeled by a stack of plates. At thermal equilibrium, the heat flux conducted is the same through all the plates in the stack. The skin temperature under the epidermis and dermis layers 660 can be calculated based on one-dimensional Fourier's law with the following equation:

$$T\_armpit = q\Delta x'/K' + T1 \qquad \text{eqn (2)}$$

where T_armpit (shown in FIG. 6) is the skin temperature under the epidermis and dermis layers 660; K' is the composite thermal conductivity of the above described layers, T1 is the temperature measured by the temperature sensor 601A at the bottom and the top surfaces of the plate 602, while $\Delta x'$ is the total thickness of these layers.

Equations (1) and (2) show that when the pair of the temperature sensors 601A and 601B are used to measure temperature across the plate 602, the measurement value of T_armpit is minimally impacted by the thermal environment above the elastic layer 520. In other words, when arm is opened, the heat convection in the air has little influence on the measurement of T_armpit.

The calculations described in equations (1) and (2) above can be conducted by the controller 514 or an external device wirelessly connected with the improved wearable thermometer patch 500 via the Bluetooth chip 512. The controller 514 can receive temperature measurement data from the temperature sensors 601A and 601B via the circuit in the substrate 510.

When arm is opened or closed, however, the thermal contact resistance between the bottom of the metal cup 604 and the epidermis and dermis layers 660 may vary. The integrated force sensor 530 can measure the contact force, which correlates with the thermal contact resistance. Thus, using a combination of DTS and a force sensor, a more accurate temperature can be obtained from the armpit by eliminating impacts from the ambient temperature and the compressing force and the variations in the contact force.

Figure 7:
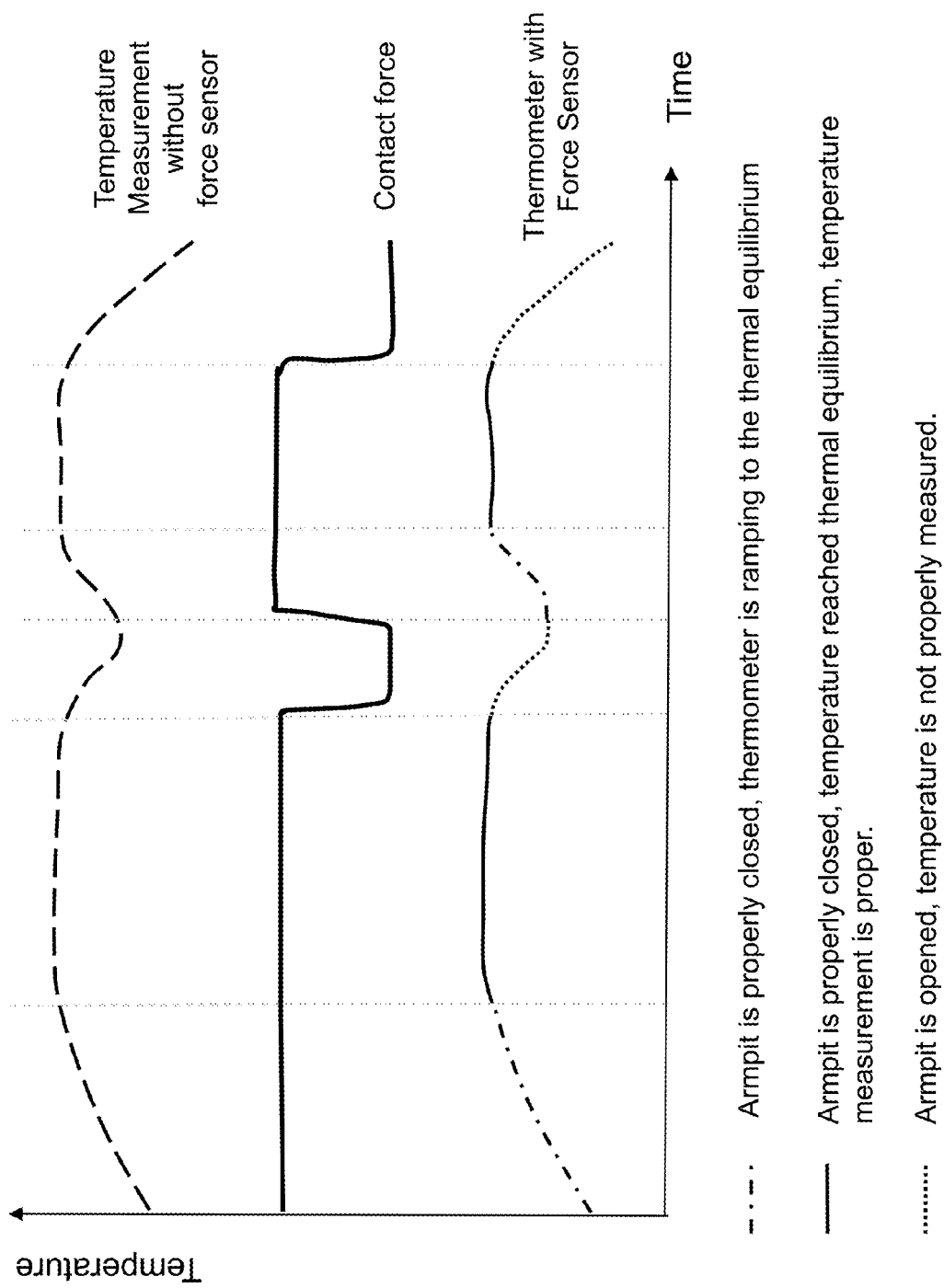
FIG. 7 illustrates time series of temperature and force measurement data and segmentation of the temperature measurement data based on the force measurement data.

Referring to FIG. 7, the upper curve shows a time series of temperatures measured without contact force measurement, which shows unknown variations in temperature values, which are sources of measurement inaccuracies. The curve in the middle shows a time series of contact forces measured by the above described force sensor, which shows variations in the contact force, which is caused by the open and close of the armpit during measurements. The lower curve shows a time series of temperature measurement being segmented according to the open/close status of the armpit as interpreted by the contact force measurement by the force sensor: a) the dotted-dashed lines show the status when the armpit is properly closed and thermometer is ramping to the thermal equilibrium; b) the solid lines show that armpit is properly closed, the temperature have reached thermal equilibrium, and the temperature measurements are proper; and c) the dotted lines correspond to the period when the armpit is opened, temperature is not properly measured, and the temperature measurement data should be discarded. The temperature measurement of user's skin can thus be drastically improved by using data obtained from only the periods when there are good thermal contacts between the improved wearable thermometer patch 500 and the user's skin.

The above described segmentation and selection of the time series of the temperature measurement data based on force sensing data can be conducted by the controller 514 or an external device wirelessly connected with the improved wearable thermometer patch 500 via the Bluetooth chip 512. The controller 514 can receive temperature measurement data from the force sensor 530 via the circuit in the substrate 510.

The disclosed wearable thermometer patches can also include electronic components such as the semiconductor chips, resistors, capacitors, inductors, diodes (including for example photo sensitive and light emitting types), other types of sensors, transistors, amplifiers. The sensors can also measure temperature, acceleration and movements, and chemical or biological substances. The electronic components can also include electromechanical actuators, chemical injectors, etc. The semiconductor chips can perform communications, logic, signal or data processing, control, calibration, status report, diagnostics, and other functions.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention.

What is claimed is:

1. A wearable thermometer patch, comprising:
   a substrate;
   a temperature probe unit mounted in the substrate and configured to measure temperature of a user's skin, wherein the temperature probe unit comprises:
      a thermally conductive cup having a bottom portion mounted in an opening of the substrate;
      a force sensor configured to measure contact force between the temperature probe unit and the user's skin;
      a plate;
      a first temperature sensor attached to a lower surface of the plate; and
      a second temperature sensor attached to an upper surface of the plate;
   a thermally-conductive adhesive attached to the temperature probe unit and configured to conduct heat between the temperature probe unit and the user's skin, wherein the thermally-conductive adhesive affixes the first temperature sensor, the second temperature sensor, and the plate to an inner surface of the thermally conductive cup; and
   an adhesive layer under the substrate, the adhesive layer configured to attach to human skin.

2. The wearable thermometer patch of claim 1, wherein the substrate comprises an electric circuit that is electrically connected to the first temperature sensor, the second temperature sensor, and the force sensor.

3. The wearable thermometer patch of claim 1, further comprising:
   a controller mounted on the substrate and in electric connection with the first temperature sensor and the second temperature sensor, and the force sensor,
   wherein the first temperature sensor and the second temperature sensor are respectively configured to measure a first time series of temperature values and a second time series of temperature values, wherein the controller is configured to calculate the temperature of the user's skin by discarding at least a portion of the temperature values in the first time series of temperature values and the second time series of temperature values based on the contact force measured by the force sensor.

4. The wearable thermometer patch of claim 1, further comprising:
   a thermally insulating material in a top portion of the thermally conductive cup, wherein the force sensor is positioned on the thermally insulating material and the thermally conductive cup.

5. The wearable thermometer patch of claim 1, further comprising:
   a controller mounted on the substrate and in electric connection with an electric circuit, wherein the controller is configured to receive first electric signals from the first temperature sensor and the second temperature sensor in response to respective temperature measurements, wherein the controller is configured to receive second electric signals from the force sensor in response to measurement of the contact force.

6. The wearable thermometer patch of claim 5, wherein the controller is configured to calculate the temperature of the user's skin using a difference between temperature measurements from the first temperature sensor and the second temperature sensor.

7. The wearable thermometer patch of claim 5, wherein the controller is configured to segment a time series of the temperature measurements from the first temperature sensor and the second temperature sensor based on the second electric signals received from the force sensor.

8. The wearable thermometer patch of claim 7, wherein the controller is configured to calculate the temperature of the user's skin by discarding at least a portion of the temperature values in the first time series of temperature values and the second time series of temperature values based on the contact force measured by the force sensor.

9. The wearable thermometer patch of claim 5, further comprising:
an antenna in electric connection with the semiconductor chip and configured to wirelessly send measured temperature values and contact force values to an external device.

10. The wearable thermometer patch of claim 1, further comprising:
electronic components mounted or formed on the substrate and in electric connection with an electric circuit, wherein the electronic components comprise a semiconductor chip, an antenna, a battery, or a bonding pad.

11. The wearable thermometer patch of claim 1, further comprising:
an elastic layer formed on the substrate and the temperature probe unit.

12. A wearable thermometer patch, comprising:
a substrate comprising an opening; and
a temperature probe unit mounted in the opening of the substrate, wherein the temperature probe unit is configured to measure temperature of a user's skin, wherein the temperature probe unit includes a thermally conductive bottom portion,
wherein the temperature probe unit includes:
a plate;
a first temperature sensor attached to a lower surface of the plate;
a second temperature sensor attached to an upper surface of the plate; and
a thermally-conductive adhesive that fixes the first temperature sensor, the second temperature sensor, and the plate to the thermally conductive bottom portion to conduct heat between the temperature probe unit and the user's skin.

13. The wearable thermometer patch of claim 12, wherein the temperature probe unit includes a thermally conductive cup comprising the bottom portion.

14. The wearable thermometer patch of claim 13, further comprising:
a thermally insulating material above the temperature probe unit in the thermally conductive cup.

* * * * *